United States Patent
Smith et al.

(10) Patent No.: US 7,176,334 B2
(45) Date of Patent: Feb. 13, 2007

(54) PROCESS FOR THE PREPARATION OF SUBSTITUTED HALOGENATED ANILINE

(75) Inventors: Jonathan O. Smith, Beaumont, TX (US); Melissa A. Petruska, Los Alamos, NM (US); Jon J. Longlet, Nederland, TX (US)

(73) Assignee: BASF Aktiengesellschaft, Ludwigshagen (DE)

( * ) Notice: Subject to any disclaimer, the term of this patent is extended or adjusted under 35 U.S.C. 154(b) by 73 days.

(21) Appl. No.: 10/537,801

(22) PCT Filed: Dec. 16, 2003

(86) PCT No.: PCT/EP03/14354

§ 371 (c)(1), (2), (4) Date: Jun. 7, 2005

(87) PCT Pub. No.: WO2004/054961

PCT Pub. Date: Jul. 1, 2004

(65) Prior Publication Data

US 2006/0116533 A1     Jun. 1, 2006

Related U.S. Application Data

(60) Provisional application No. 60/433,847, filed on Dec. 16, 2002.

(51) Int. Cl.
*C07C 211/00* (2006.01)
*C07C 291/00* (2006.01)

(52) U.S. Cl. .................. 564/442; 564/305; 564/248; 564/270

(58) Field of Classification Search .............. 564/248, 564/270, 305, 442
See application file for complete search history.

(56) References Cited

U.S. PATENT DOCUMENTS 5,965,775 A    10/1999    Pfirmann et al.

FOREIGN PATENT DOCUMENTS

| EP | 0 878 461 A | 11/1998 |
| WO | WO 00 69805 A | 11/2000 |

*Primary Examiner*—Thurman K. Page
*Assistant Examiner*—Yevgeny Valenrod
(74) *Attorney, Agent, or Firm*—Rothwell, Figg, Ernst & Manbeck, P.C.

(57) ABSTRACT

A process for the preparation of substituted halogenated anilines from substituted halogenated 1-chlorobenzenes which comprises a) reacting a substituted halogenated 1-chlorobenzene selectively with an imine in the presence of a transition metal catalyst complex and a base to form an N-aryl imine; b) hydrolyzing the N-aryl imine; and c) isolating the substituted halogenated aniline.

19 Claims, No Drawings

PROCESS FOR THE PREPARATION OF SUBSTITUTED HALOGENATED ANILINE

CROSS REFERENCE TO RELATED APPLICATION

This application is a 35 USC § 371 National Phase Entry Application from PCT/EP2003/014354, filed Dec. 16, 2003, and designating the United States, which claims the benefit of Provisional Application No. 60/433,847 filed Dec. 16, 2002.

This invention relates to a method for the preparation of substituted halogenated anilines from substituted halogenated 1-chlorobenzenes, especially to substituted fluoroanilines from substituted 1-chlorofluorobenzenes.

For Example 3,5-difluoroaniline is used in the synthesis of important agricultural compounds such as diflufenzopyr. The currently available synthetic procedures for 3,5-difluoroaniline are expensive and corrosive. One synthesis uses the expensive 2,4-difluoroaniline as a starting material. Other synthetic routes are also high cost because they either involve expensive reagents or have low yields. As a result there is a need for a more economic commercial process to produce this intermediate.

This invention relates to a method for the preparation of substituted halogenated anilines from substituted halogenated chlorobenzenes, especially substituted fluoroanilines from substituted 1-chlorofluorobenzenes in high yield. The substituted halogenated anilines are prepared by selectively reacting the chlorine of the substituted halogenated 1-chlorobenzene and an imine in the presence of a transition metal catalyst complex to form an N-aryl imine that is then transformed with or without isolation to the corresponding primary amine.

The process of the instant invention can be represented by the generalized reaction depicted in Scheme I.

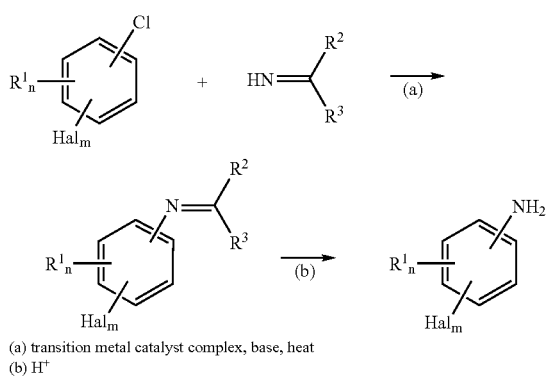

(a) transition metal catalyst complex, base, heat
(b) H⁺ wherein
$R^1$ is halogen, $C_1$–$C_6$ alkyl, $C_2$–$C_6$ alkenyl, $C_1$–$C_6$ alkoxy, $C_3$–$C_6$ cycloalkyl, $C_3$–$C_6$ cycloalkyl $C_1$–$C_6$alkyl or aryl;
$R^2$, $R^3$ are aryl;
Hal is fluorine or chlorine;
m is 1 or 2; and
n is 1 or 2.

Suitable transition metal catalysts include soluble or insoluble complexes of platinum, palladium and nickel. Nickel and palladium are particularly preferred and palladium is most preferred. The metal center of palladium catalysts Is desirably in the zero-valent state or is capable of being reduced to metal (0). Suitable soluble palladium complexes include, but are not limited to, tris(dibenzylideneacetone) dipalladium [$Pd_2(dba)_3$], bis(dibenzylideneacetone) dipalladium [$Pd(dba)_2$] and palladium acetate.

Catalyst complexes may comprise chelating ligands, like alkyl and aryl derivatives of phosphines and bisphosphines, imines, arsines, and hybrids thereof, including hybrids of phosphines with amines. The phosphines can be monodentate phosphine ligands, like trimethylphosphine, triethylphosphine, tripropylphosphine, triisopropylphosphine, tributylphosphine, tricyclohexylphosphine, trimethylphosphite, trethyl phosphite, tripropyl phosphite, triisopropylphosphite, tributyl phosphite and tricyclohexylp phosphite, in particular triphenylphosphine, tri(o-toyl)phosphine, triisopropylphosphine or tricyclohexylphosphine; or a bidentate phosphine ligand such as 2,2'-bis(diphenylphosphino)-1,1'-binaphthyl (BINAP), 1,2-bis(dimethylphosphino)ethane, 1,2-bis(diethylphosphino)ethane, 1,2-bis(dipropylphosphino)ethane, 4,5-bis(diphenylphosphino)-9,9-dimethylxanthene (xant-phos), 1,1'-bis(diphenylphosphino)ferrocene (dppf), bis(2-(diphenylphosphino)phenyl)ether [DPE-phos], 1,2-bis(diisopropylphosphino)ethane, 1,2-bis(dibutylphosphino)ethane, 1,2-bis(dicyclohexylphosphino)ethane, 1,3-bis(diisopropylphosphino)propane, 1,3-bis(dicyclohexylphosphino)propane, 1,4-bis(diisopropylphosphino)butane, 1,4-bis(dicyclohexylphosphino)butane, 1,4-bis(diphenylphosphino)butane (bppb) and 2,4-bis(dicyclohexylphosphino)pentane. Also ligands comprising Lewis basic nitrogen atoms may be included in the transition metal catalyst, e.g. 1,10-phenanthroline and the like. Preferred are 1,10-phenanthroline and the like. Preferred are 1,1'-bis(diphenylphosphino)ferrocene (dppf) and 1,4-bis(diphenylphosphino)butane (bppb).

Suitable bases are selected from the group consisting of alkoxides, carbonates, bicarbonates, hydroxides, amides, amines, phosphates and fluorides. Especially the base is selected from an alkoxide such as sodium tert-butoxide, potassium tert-butoxide, sodium methoxide; an alkali metal amide such as sodium amide, lithium diisopropylamide or an alkali metal bis(trialkylsilyl)amide such as lithium bis-(trimethyl-silyl)amide or sodium bis-(trimethyl-silyl)amide, a tertiary amine such as triethylamine, trimethylamine, N,N-dimethylaminopyridine, 1,5-diazabicycl[4.3.0]nonene-5 (DBN), 1,5-diazabicycl-[5.4.0]undecene-5 (DBU) as well as an alkali, alkaline earth carbonate, bicarbonate or hydroxide such as sodium, magnesium, calcium, barium, potassium, or cesium carbonate, hydroxide or bicarbonate. Preferred is sodium tert-butoxide.

The acid used to cleave the imine is preferably an aqueous inorganic acid such as hydrochloric acid, or sulphuric acid.

Alternatively, the reaction to cleave the N-aryl imine and form the desired aniline is carried out by other procedures known in the art.

In a preferred embodiment the radical $R^1$ of the substituted halogenated anilines is halogen, like fluorine or chlorine, $C_1$–$C_6$ alkyl, like methyl or ethyl or $C_2$–$C_6$ alkenyl, like vinyl or allyl; especially $R^1$ is halogen, like fluorine or chlorine, or $C_1$–$C_6$ alkyl, like methyl; preferably $R^1$ is fluorine, chlorine or methyl.

In another preferred embodiment the radicals $R^2$ and $R^3$ of the substituted halogenated anilines are phenyl or naphthyl, especially phenyl.

In another preferred embodiment m is 1 and n is 1 or 2.

In another preferred embodiment Hal is linked in meta position to the phenyl moiety (with regard to the amino group) and m is 1.

In another preferred embodiment the base used in the first step of the reaction is preferably an alkali or earth alkaline alkoxide or an alkali or earth alkaline carbonate, most preferably sodium tert-butoxide.

In another preferred embodiment the N-aryl imine is isolated and purified.

In another preferred embodiment the N-aryl imine is reacted in the second step without isolation or purification.

The term "aryl" refers to a group that contains one or more aromatic rings, for example, phenyl or naphthyl, which are unsubstituted or partially or fully halogenated and/or may carry one to three of the following radicals: nitro, cyano, $C_1$–$C_4$ alkyl, $C_1$–$C_4$ haloalkyl, $C_1$–$C_4$ alkoxy or $C_1$–$C_4$ haloalkoxy. In a preferred embodiment "aryl" refers to phenyl.

The reaction is generally carried out in an inert solvent, preferably one in which the reaction ingredients, including the catalyst, are substantially soluble. Suitable solvents include ethers such as diethyl ether, 1,2-dimethoxy ethane, diglyme, t-butyl methyl ether, tetrahydrofuran, and the like, aliphatic or aromatic hydrocarbon solvents such as benzene, xylene, toluene, hexane, pentane and the like, esters such as ketones such as ethyl acetate, acetone and 2-butanone; polar aprotic solvents such as aceotnitrile, di-methylsulfoxide, dimethylformamide and the like; or combinations of two or more solvents.

The reaction is typically carried out in the temperature range of from about 25° C. to about 300° C., more preferably in the range of from about 25° C. to about 150° C.

In certain embodiments it is preferable to perform the reactions under an inert atmosphere of a gas such as nitrogen or argon, preferably nitrogen.

In a preferred embodiment Hal and $R^1$ are both chlorine or fluorine; especially m and n are both 1; in particular these radicals are linked in meta/meta' position to the phenyl moiety (with regard to the amino group).

In another preferred embodiment Hal is chlorine or fluorine and $R^1$ is $C_1$–$C_6$ alkyl, especially methyl; especially m and n are both 1; preferably Hal is linked in meta position to the phenyl moiety (with regard to the amino group); in particular $R^1$ is linked in ortho position to the phenyl moiety (with regard to the amino group).

In another preferred embodiment the imine is benzophenone imine.

In another preferred embodiment, this invention relates to a method for the preparation of 3,5-difluoroaniline from 1-chloro-3,5-difluorobenzene. More particularly the invention comprises reacting 1-chloro-3,5-difluorobenzene with benzophenone imine in the presence of a palladium catalyst and a ligand such as 1,1'-bis(diphenylphosphino)ferrocene (dppf) or 1,4-bis-diphenylphosphinobutane (dppb) to form an intermediate imine which is then reacted, without isolation or purification, with acid to obtain the desired 3,5-difluoroaniline.

In another preferred embodiment, this invention relates to a method for the preparation of 3,5-dichloroaniline from 1,3,5-trichlorobenzene. More particularly the invention comprises reacting 1,3,5-trichlorobenzene with benzophenone imine in the presence of a palladium catalyst and a ligand such as 1,1'-bis(diphenylphosphino)ferrocene (dppf) or 1,4-bis-diphenylphosphinobutane (dppb) to form an intermediate imine which is then reacted, without isolation or purification, with acid to obtain the desired 3,5-dichloroaniline.

In another preferred embodiment, this invention relates to a method for the preparation of 3-chloro-2-methylaniline from 2,6-dichlorotoluene. More particularly the invention comprises reacting 2,6-dichlorotoluene with benzophenone imine in the presence of a palladium catalyst and a ligand such as 1,1'-bis(diphenylphosphino)ferrocene (dppf) or 1,4-bis-diphenylphosphinobutane (dppb) to form an intermediate imine which is then reacted, without isolation or purification, with acid to obtain the desired 3-chloro-2-methylaniline.

EXAMPLE 1

3,5-Difluoroaniline

A 4-neck, 500 mL flask was equipped with a mechanical stirrer, a glass stopper, a rubber septum and a condenser with an inert gas inlet. To this flask was added, in order, tris (dibenzylideneacetone)dipalladium (0) ($Pd_2(dba)_3$) (25 mg, 0.01 mol %), 1,1'-bis(diphenylphosphino)ferrocene (dppf) (46 mg, 0.03 mol %), sodium tert-butoxide (37 g, 1.4 eq, xylenes (90 mL), 1-chloro-3,5-difluorobenzene (49.2 g, 0.33 mol) and benzophenone imine (50 g, 0.28 mol). The mixture was refluxed for 8 hours until GC analysis confirmed that the benzophenone imine had been consumed. The reaction mixture was cooled slightly, and 150 mL of 2M HCl was added slowly to the reaction mixture with some gas evolution and the mixture was refluxed with sufficient agitation for 45 minutes. While still warm, the reaction mixture was put in a separatory funnel and the aqueous layer was collected. An additional 90 mL of xylenes was added to the separatory funnel and the organic layer was washed with 4×100 mL 1M HCl. The acidic fractions were combined and made alkaline with aqueous conc ammonium hydroxide. The free amine was extracted with 250 mL methyl tert-butyl ether. The organic layer was dried over magnesium sulfate and concentrated in vacuo to yield the expected product in 89% yield.

EXAMPLE 2

3,5-dichloroaniline

A 50 mL 3 neck round bottom flask was oven dried, cooled under nitrogen, and charged with 14.50 g of xylenes. The flask was then charged with 1,3,5-trichlorobenzene (9.760 g, 53.49 mmol), benzophenone imine (7.620 g, 42.04 mmol), $(dba)_3Pd_2$ catalyst (0.023 g, 0.03 mmol in 2 g xylene), dppf ligand (0.042 g, 0.08 mmol in 2.g xylene) and sodium t-butoxide (5.550 g, 57.70 mmol). The reaction mixture was heated to reflux (136° C.) for 3 hours and then cooled to room temperature. The aromatic imine intermediate was then hydrolyzed with 22 mL of 2 N HCl (aq) at 70° C. for 45 minutes. The hydrochloride salt of dichloroaniline precipitated out of solution when cooled to room temperature. The crude hydrochloride salt was collected by filtration using a buchner funnel and then washed with methyl-tert. butyl ether. The dichloroanaline salt was then added to 30 mL of methyl-tert. butyl ether and pH adjusted to 12 using 50% NaOH. The methyl-tert. butyl ether phase was collected and then stripped under vacuum to give 3,5-dichloroaniline in 86% yield.

EXAMPLE 3

3-chloro-2-methylanaline

A 50 mL 3 neck round bottom flask was oven dried, cooled under nitrogen, and charged with 18.6 grams of xylenes. The flask was then charged with 2,6-dichlorotoluene (7.995 g, 49.65 mmol), benzophenone imine (7.612 g, 42.0 mmol), (dba)$_3$Pd$_2$ catalyst (0.023 g, 0.025 mmol in 2.27 g xylene), dppf ligand (0.042 g, 0.08 mmol in 2.53 g xylene) and sodium t-butoxide (5.689 g, 59.19 mmol). The reaction was heated to 125° C. for 6 hrs and then cooled to room temperature. The aromatic imine intermediate was hydrolyzed with 2 N HCl (aq) at 65° C., cooled to room temperature, and then transferred to a separatory funnel. The aqueous phase was collected and the organic phase was extracted 2 more times with 2 N HCl. The aqueous phases were then combined with 20 mL of methyl tert.-butyl ether and treated with 50% NaOH (aq) to pH of 11. The aqueous phase was then extracted 2 more times with 20 mL of methyl tert.-butyl ether. The methyl tert.-butyl ether phases were combined and stripped under stripped under vacuum to give 3-choro-2-methylanalaline in 75.5% yield in a purity of 97.7% GC-MS.

The invention claimed is:

1. A process for the preparation of a substituted halogenated 1-chlorobenzene, the process comprising
    (a) reacting a substituted halogenated 1-chlorobenzene with an imine in the presence of a transition metal catalyst and a base to form an n-aryl imine; and
    (b) hydrolyzing the N-aryl imine to form a substituted halogenated aniline.

2. The process of claim 1 wherein the substituted halogenated 1-chlorobenzenes has the structure

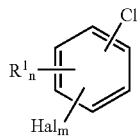

wherein
R$^1$ is halogen, C$_1$–C$_6$ alkyl, C$_2$–C$_6$ alkenyl, C$_1$–C$_6$ alkoxy, C$_3$–C$_6$ cycloalkyl, C$_3$–C$_6$ cycloalkyl C$_1$–C$_6$alkyl or aryl;
Hal is fluorine or chlorine;
m is 1 or 2; and
n is 1 or 2.

3. The process of claim 2 wherein the imine has the structure

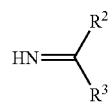

wherein
R$^2$, R$^3$ are independently aryl.

4. The process of claim 2, wherein
R$^1$ is halogen or C$_1$–C$_6$-alkyl;
m is 1;
n is 1 or 2.

5. The process of claim 2, wherein the substituted halogenated 1-chlorobenzenes is 1-chloro-3,5-difluorobenzene.

6. The process of claim 2, wherein the substituted halogenated 1-chlorobenzenes is 1,3,5-trichlorobenzene.

7. The process of claim 2, wherein the substituted halogenated 1-chlorobenzenes is 2,6-dichlorotoluene.

8. The process of claim 1, wherein the base is an alkoxide salt.

9. The process of claim 8 wherein the alkoxide salt is sodium tert-butoxide.

10. The process of claim 1, wherein the transition metal catalyst complex is a platinum, palladium or nickel complex.

11. The process of claim 10, wherein the transition metal catalyst complex comprises a chelating ligand.

12. The process of claim 10, wherein the chelating ligand is a alkyl or aryl derivative of a phosphine or bisphosphine.

13. The process of claim 11, wherein the transition metal catalyst complex is Pd$_2$(dba)$_3$/dppf or Pd$_2$(dba)$_3$/dppb.

14. The process of claim 13, wherein the transition metal catalyst complex is Pd$_2$(dba)$_3$/dppf.

15. The process of claim 13, wherein the transition metal catalyst complex is Pd$_2$(dba)$_3$/dppb.

16. The process of claim 1, including the further step of isolating the substituted halogenated aniline.

17. A process for the preparation of 3,5-difluoroaniline comprising:
    a) reacting 1-chloro-3,5-difluorobenzene with benzophenone in the presence of a palladium catalyst complex which comprises 1,1'-bis(diphenylphosphino) ferrocene (dppf) or 1,4-bis-diphenylphosphinobutane (dppb) to form an intermediate imine; and
    (b) hydrolyzing with acid the intermediate imine to form 3,5-difluoroanline.

18. A method for the preparation of 3,5-dichloroaniline comprising:
    a) reacting 1,3,5-trichlorobenzene with benzophenone imine in the presence of a palladium catalyst complex which comprises 1,1-bis(diphenylphosphino) ferrocene (dppf) or 1,4-bis-diphenylphosphinobutane (dppb) to form an intermediate imine: and
    (b) hydrolyzing with acid the intermediate imine to form 3,5-dichloroaniline.

19. A process for the preparation of 3-chloro-2-methylaniline comprising;
    (a) reacting 2,6-dichlorotoluene with benzophenone imine in the presence of a palladium catalyst complex which comprises 1,1'-bis(diphenylphosphino) ferrocene (dppf) or 1,4-bis-diphenylphosphinobutane (dppb) for form an intermediate imine; and
    (b) hydrolyzing with acid the intermediate imine to form 3-chloro-2-methylaniline.

* * * * *